United States Patent [19]

Chang et al.

[11] 3,998,898
[45] Dec. 21, 1976

[54] MANUFACTURE OF GASOLINE

[75] Inventors: Clarence D. Chang, Princeton; William H. Lang, Pennington, both of N.J.; Anthony J. Silvestri, Morrisville, Pa.

[73] Assignee: Mobil Oil Corporation, New York, N.Y.

[22] Filed: July 2, 1975

[21] Appl. No.: 592,434

Related U.S. Application Data

[63] Continuation-in-part of Ser. No. 387,224, Aug. 9, 1973, Pat. No. 3,907,915.

[52] U.S. Cl. .................. 260/668 R; 260/449 R; 260/449.5; 260/671 R; 260/673; 260/673.5; 260/682; 252/455 Z; 208/141
[51] Int. Cl.² .......................................... C07C 1/20
[58] Field of Search ...... 260/668 R, 449 R, 449 M, 260/449 L, 449.5, 671 R, 673, 673.5, 682; 208/141; 252/455 Z

[56] References Cited

UNITED STATES PATENTS 3,907,915  9/1975  Chang et al. .................. 260/668 R

*Primary Examiner*—Veronica O'Keefe
*Attorney, Agent, or Firm*—C. A. Huggett; M. G. Gilman

[57] ABSTRACT

Reacting mixtures of difficultly convertible aliphatic organic oxygenate compounds, such as short chain aldehydes, carboxylic acids or carbohydrates with easily convertible aliphatic alcohols, ethers, acetals and analogs thereof over a crystalline aluminosilicate zeolite having a silica to alumina ratio of at least about 12 and a constraint index of about 1 to 12, at elevated temperatures, 0.5 to 50 LHSV and 1 to 200 atmospheres to produce a product comprising water, full range highly aromatic hydrocarbon gasoline and light aliphatic hydrocarbon gases having an improved production of $C_6$ and $C_{10}$ monocyclic aromatic hydrocarbons.

8 Claims, 1 Drawing Figure

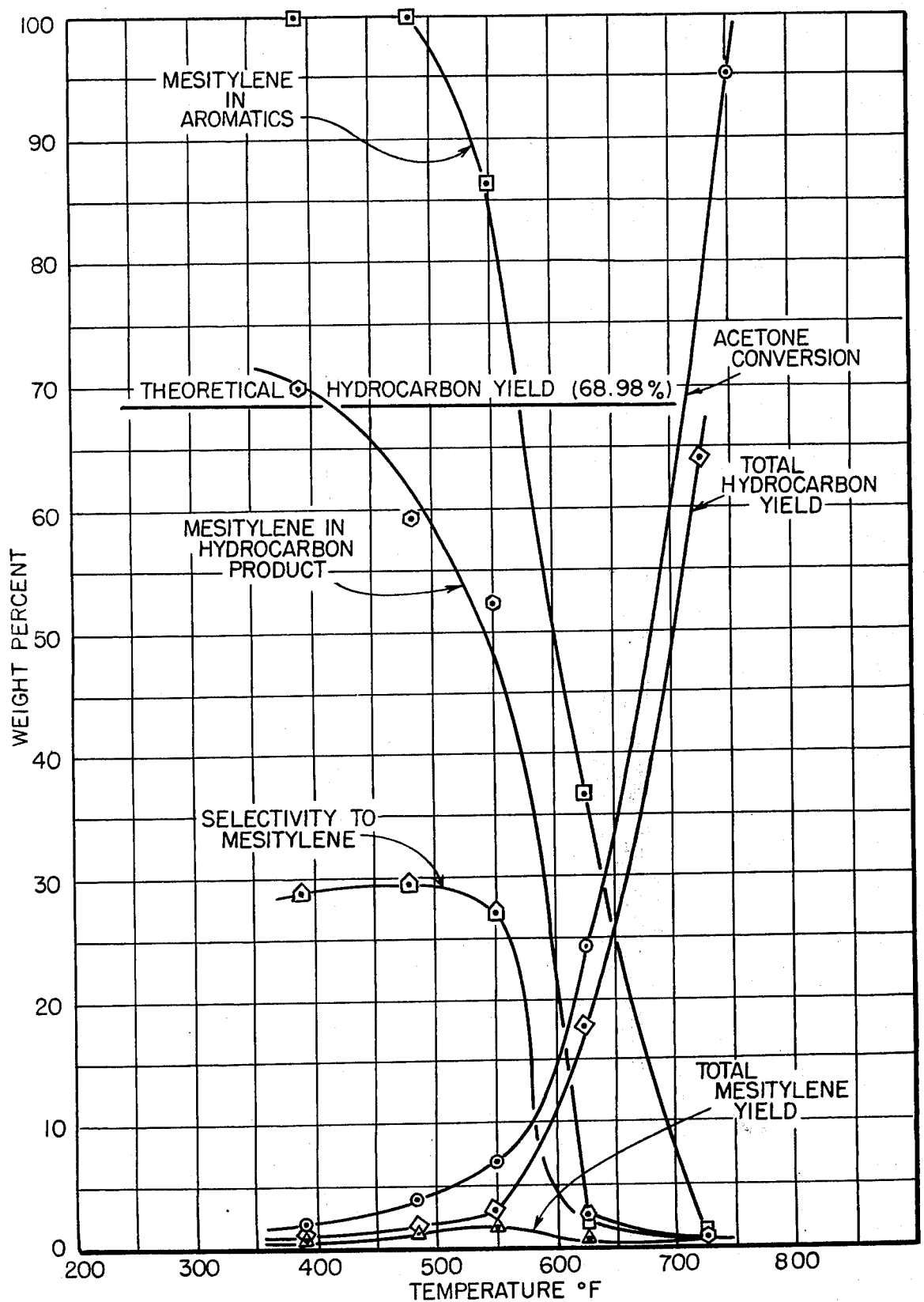

MANUFACTURE OF GASOLINE

This application is a continuation-in-part of application Ser. No. 387,224 filed Aug. 9, 1973, now U.S. Pat. No. 3,907,915.

This invention relates to the synthetic production of gasoline. It more particularly refers to an improved method of converting simple organic chemicals, particularly certain mixtures thereof to hydrocarbons boiling in the gasoline boiling range.

Gasoline, as such term is used in the instant specification, and as such term is commonly used in the petroleum industry, is a motor fuel for internal combustion engines. It is hydrocarbon in nature being composed of various aliphatic and aromatic hydrocarbons having a full boiling range of about $C_5$ to about 280° to 430° F. depending upon the exact blend used and the time of the year. Although gasoline is predominantly hydrocarbon in nature, various additives which are not necessarily exclusively hydrocarbon are often included. Additives of this type are usually present in very small proportions, e.g. less than 1% by volume of the total gasoline. It is also not uncommon for various gasolines to be formulated with non-hydrocarbon components, particularly alcohols and/or ethers, as significant although not major, constituents thereof. Such alcohols, ethers and the like have burning qualities in internal combustion engines which are similar to those of hydrocarbons in the gasoline boiling range. For purposes of this application, the term "gasoline" is used to mean a mixture of hydrocarbons boiling in the aforementioned gasoline boiling range and is not intended to mean the above-referred to additives and/or non-hydrocarbon constituents.

It is generally known that various specific hydrocarbon compounds or isomeric mixtures of hydrocarbon compounds boiling in the gasoline boiling range can be made by converting various appropriate organic chemicals using specific processes particularly adapted to the particularly desired conversion. Thus, for example, acetone can be converted to mesitylene over many different acid catalysts, including acid zeolites. Propylene can be converted to 2-ethyl hexane by a combination of hydroformylation, hydrogenation and Aldol condensation, using a metal catalyst in a basic system, through an aldehyde and/or alcohol intermediate (butyraldehyde and 2-ethyl hexanol). Similarly, acetaldehyde can be converted to iso-octane by Aldoling and hydrogenolysis. Methanol can be converted to toluene by alkylation of benzene using an acid zeolite catalyst.

It is clear, however, that all of the known processes of this type do not produce a wide range of hydrocarbon products, and do not even produce significant quantities of full range gasoline. U.S. Pat. No. 2,950,332, Mattox, discloses the use of crystalline aluminosilicate zeolites as catalysts to convert ketones to aromatics, particularly acetone to mesitylene. In particular, rather low silica to alumina ratio zeolites, such as Y, were employed by this patentee. His reaction temperatures were about 300° to 900° F. and he produced as much as about 43% $C_9^+$ aromatics from acetone at 500° F.

U.S. Pat. No. 3,728,408, Tobias, carried this conversion over into the use of high silica to alumina ratio zeolites, such as dealuminized Y and ZSM-5. Tobias insisted upon a minimum silica to alumina ratio of 10 and showed a 25% conversion of acetone to mesitylene and mesityl oxide using a 17 to 1 silica to alumina ratio ZSM-5 at 200° C. (392° F.). The ratio of mesityl oxide to mesitylene in Tobias' product was reported to be 9 to 1. This calculates out to a yield of 2.07% (by wt) mesitylene based upon acetone feed. As noted in the prosecution of the above-referred to parent application, consideration of the gas chromatograph of Tobias' product fails to show the production of any aromatic hydrocarbon, or in fact any hydrocarbon, other than mesitylene.

U.S. Pat. No. 2,456,584 is also worthy of note, for reasons which will become apparent below, because it discloses the conversion of dimethylether to hydrocarbon gasoline using a silica alumina catalyst. This reference indicates that while dimethyl ether by itself is poorly converted to gasoline, in admixture with isobutane, the mixture converts very nicely to aromatic gasoline.

With all this prior art at his disposal, the routineer in the chemical arts still does not known how to convert relatively simple hetero-atom containing organic chemicals directly to hydrocarbon gasoline, particularly full range gasoline, of commercial quality and in commercial quantity.

It is, therefore, an object of this invention to provide an improved means of converting relatively simple organic compounds to gasoline.

It is another object of this invention to provide a novel means of converting certain lower, aliphatic carbonyl containing organic compounds and carbohydrates to gasoline.

It is a further object of this invention to provide a novel means of converting organic chemical streams containing carbonyl compounds to hydrocarbon gasoline.

Other and additional objects of this invention will be apparent from a consideration of this entire specification including the claims hereof.

In accord with and fulfilling these objects, one aspect of this invention resides in a process comprising contacting a mixture of a difficulty convertible lower aliphatic organic chemical containing oxygen and an easily convertible lower organic aliphatic organic chemical containing oxygen with a catalyst comprising a crystalline aluminosilicate zeolite having a silica to alumina ratio of at least 12, a constraint index of about 1 to 12, and preferably a crystal density of not substantially below about 1.6 grams per cubic centimeter; under reaction conditions of elevated temperature of at least about 500° F, low space velocity of about 0.5 to 50 LHSV and a pressure of about 1 to 200 atmospheres.

It will be appreciated that within the ranges of operating parameters recited will exist certain combinations of conditions which will direct the conversion toward specific types of products.

Therefore, it is appropriate to indicate that in addition to the temperature specified above as a critical variable, there is also a critical variable in the severity of operation as well as a preferred critical variable in the mode of operation. Within the operating parameters specified above, there are a number of combinations of temperature and residence time, sometimes reported as space velocity in a continuous system, which in combination define the severity required to achieve a given desired result. Since there is no generally accepted unit or numerical designation for severity, it is believed appropriate in this situation to define severity in terms of product composition; that is that combination of temperature, pressure and contact time which will yield a product in which the major proportion, based on the carbon contained in the feed, of the carbon is in the form of hydrocarbons, the preponderant components of which are $C_6$ to $C_{10}$ monocyclic aromatic hydrocarbons.

Consideration of the data presented in this specification indicates that a wide variety of hydrocarbon compounds are produced by the process hereof and that some if not most, of them are not predictable from the specified reactant by any classical chemical conversion theory or mechanism.

It is remarkable that when carrying out the process of this invention under any given set of reaction conditions, it does not seem to particularly matter what reactant or reactant mixture is chosen, the product slate seems to be just about the same, e.g. ethyl acetate gives just about the same products as does acetone. This appears to be a qualitative fact, that is that the product slate produced is substantially equivalent. There are differences in proportion of individual constituents of the product slate as a function of the particular reactant conditions chosen, but the product slate appears to remain substantially unaltered. In fact, it would appear that the product slate is not a function of any specific reactant. Under equivalent operating conditions, substantially the same product results regardless of which specific reactants are used.

The special zeolite catalysts referred to herein utilize members of a special class of zeolites exhibiting some unusual properties. These zeolites induce profound transformations of aliphatic hydrocarbons to aromatic hydrocarbons in commercially desirable yields and are generally highly effective in alkylation, isomerization, disproportionation and other reactions involving aromatic hydrocarbons. Although they have unusually low alumina contents, i.e. high silica to alumina ratios, they are very active even with silica to alumina ratios exceeding 30. This activity is surprising since catalytic activity of zeolites is generally attributed to framework aluminum atoms and cations associated with these aluminum atoms. These zeolites retain their crystallinity for long periods in spite of the presence of steam even at high temperatures which induce irreversible collapse of the crystal framework of other zeolites, e.g. of the X and A type. Furthermore, carbonaceous deposits, when formed, may be removed by burning at higher than usual temperatures to restore activity. In many environments, the zeolites of this class exhibit very low coke forming capability, conductive to very long times on stream between burning regenerations.

An important characteristic of the crystal structure of this class of zeolites is that it provides constrained access to, and egress from, the intra-crystalline free space by virtue of having a pore dimension greater than about 5 Angstroms and pore windows of about a size as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred zeolites useful as catalysts in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The zeolites useful as catalysts in this invention freely sorb normal hexane and have a pore dimension greater than about 5 Angstroms. In addition, their structure must provide constrained access to some larger molecules It is sometimes possible to judge from a known crystal structure whether such constrained access exists. For example, if the only pore windows in a crystal are formed by 8-membered rings of oxygen atoms, then access by molecules of larger cross-section than normal hexane is substantially excluded and the zeolite is not of the desired type. Zeolites with windows of 10-membered rings are preferred, although excessive puckering or pore blockage may render these zeolites substantially ineffective. Zeolites with windows of twelve-membered rings do not generally appear to offer sufficient constraint to produce the advantageous conversions desired in the instant invention, although structures can be conceived, due to pore blockage or other cause, that may be operative.

Rather than attempt to judge from crystal structure whether or not a zeolite possesses the necessary constrained access, a simple determination of the "constraint index" may be made by continuously passing a mixture of equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F for at least 15 minutes. The zeolite is then flushed with helium and the temperature adjusted between 550° and 950° F to give an overall conversion between 10 and 60%. The mixture of hydrocarbons is passed at 1 liquid hourly space velocity (i.e., 1 volume of liquid hydrocarbon per volume of catalyst per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Catalysts suitable for the present invention are those which employ a zeolite having a constraint index from 1.0 to 12.0. Constraint Index (CI) values for some typical zeolites including some not within the scope of this invention are:

| CAS | C.I. |
|---|---|
| ZSM-5 | 8.3 |
| ZSM-11 | 8.7 |
| ZSM-35 | 4.5 |
| TMA Offretite | 3.7 |
| ZSM-12 | 2 |
| ZSM-38 | 2 |
| Beta | 0.6 |
| ZSM-4 | 0.5 |
| Acid Mordenite | 0.5 |
| REY | 0.4 |
| Amorphous Silica-alumina | 0.6 |
| Erionite | 38 |

The above-described Constraint Index is an important and even critical, definition of those zeolites which are useful to catalyze the instant process. The very nature of this parameter and the recited technique by which it is determined, however, admit of the possibility that a given zeolite can be tested under somewhat different conditions and thereby have different constraint indexes. Constraint Index seems to vary somewhat with severity of operation (conversion). Therefore, it will be appreciated that it may be possible to so select test conditions to establish multiple constraint indexes for a particular given zeolite which may be both inside and outside the above defined range of 1 to 12.

Thus, it should be understood that the Constraint Index value as used herein is an inclusive rather than an exclusive value. That is, a zeolite when tested by any combination of conditions within the testing definition set forth herein above to have a constraint index of 1 to 12 is intended to be included in the instant catalyst definition regardless that the same identical zeolite tested under other defined conditions may give a constraint index value outside of 1 to 12.

The class of zeolites defined herein is exemplified by ZSM-5, ZSM-11, ZSM-12, ZSM-21, ZSM-35, ZSM-38, and other similar material. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

U.S. application, Ser. No. 358,192, filed May 7, 1973, the entire contents of which are incorporated herein by reference, describes a zeolite composition, and a method of making such, designated as ZSM-21 which is useful in this invention.

U.S. application Ser. No. 528,061 filed Nov. 29, 1974, the entire contents of which are incorporated herein by reference, describes a zeolite composition including a method of making it. This composition is designated ZSM-35 and is useful in this invention.

U.S. application Ser. No. 528,060 filed Nov. 29, 1974, the entire contents of which are incorporated herein by reference, describes a zeolite composition including a method of making it. This composition is designated ZSM-38 and is useful in this invention.

The x-ray diffraction pattern of ZSM-21 appears to be generic to that of ZSM-21 appears to be generic to that of ZSM-35 and ZSM-38. Either of all of these zeolites is considered to be within the scope of this invention.

The specific zeolites described, when prepared in the presence of organic cations, are substantially catalytically inactive, possibly because the intracrystalline free space is occupied by organic cations from the forming solution. They may be activated by heating in an inert atmosphere at 1000° F for 1 hour, for example, followed by base exchange with ammonium salts followed by calcination at 1000° F in air. The presence of organic cations in the forming solution may not be absolutely essential to the formation of this special type zeolite; however, the presence of these cations does appear to favor the formation of this special type of zeolite. More generally, it is desirable to activate this type zeolite by base exchange with ammonium salts followed by calcination in air at about 1000° F for from about 15 minutes to about 24 hours.

Natural zeolites may sometimes be converted to this type zeolite by various activation procedures and other treatments such as base exchange, steaming, alumina extraction and calcination, alone or in combinations. Natural minerals which may be so treated include ferrierite, brewsterite, stilbite, dachiardite, epistilbite, heulandite and clinoptiololite. The preferred crystalline aluminosilicates are ZSM-5, ZSM-11, ZSM-12, ZSM-21, ZSM-35 and ZSM-38, with ZSM-5 particularly preferred.

The zeolites used as catalysts in this invention may be in the hydrogen form or they may be base exchanged or impregnated to contain ammonium or a metal cation complement. It is desirable to calcine the zeolite after base exchange. The metal cations that may be present include any of the cations of the metals of Groups I through VIII of the periodic table. However, in the case of Group IA metals, the cation content should in no case be so large as to substantially eliminate the activity of the zeolite for the catalysis being employed in the instant invention. For example, a completely sodium exchanged H-ZSM-5 appears to be largely inactive for shape selective conversions required in the present invention.

In a preferred aspect of this invention, the zeolites useful as catalysts herein are selected as those having a crystal framework density, in the dry hydrogen form, of not substantially below about 1.6 grams per cubic centimeter. It has been found that zeolites which satisfy all three of these criteria are most desired. Therefore, the preferred catalysts of this invention are those comprising zeolites having a constraint index as defined above of about 1 to 12, a silica to alumina ratio of at least about 12 and a dried crystal density of not substantially less than about 1.6 grams per cubic centimeter. The dry density for known structures may be calculated from the number of silicon plus aluminum atoms per 1000 cubic Angstroms, as given, e.g. on page 19 of the article on Zeolite Structure by W. M. Meier. This paper, the entire contents of which are incorporated herein by reference, is included in "Proceedings of the Conference on Molecular Sieves, London, April, 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density of course must be associated with a relatively small amount of free space within the crystal, which might be expected to result in more stable structures. This free space, however, seems to be important as the locus of catalytic activity.

Crystal framework densities of some typical zeolites including some which are not within the purview this invention are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

It has been noted in the above-referred to parent application that carbonyl containing lower organic compounds in general convert according to the process of this invention to products comprising aromatic gasoline. It has now been discovered that short chain aldehydes (1 or 2 carbon atoms), carboxylic acids and anhydrides, glycols, glycerin, and carbohydrates, although they do convert to highly aromatic gasoline as described in the parent application, convert in a less satisfactory manner with poorer catalyst cycle life. It has been found, and it is a most important aspect of this invention, that these difficultly convertible feeds can be converted to desired product mixtures, particularly highly aromatic full range gasoline, in a synergistically better manner if the conversion is carried out as aforesaid but with a mixture of these difficultly convertible oxygenates and an easily converted oxygenate such as alcohols, ethers, esters, long chain aldehydes, ketones and their analogues.

The difficulty convertible oxygenate feeds seem to fall into certain categories of organic compounds. This categorization is empirical rather than theoretical. As noted, carboxylic acids and anhydrides, carbohydrates such as starch and sugars, lower glycols, glycerin, and other polyols and short chain aldehydes seem to be difficult to convert to a desirable product with an acceptable catalyst life. Organic carboxylic acids of any chain length are difficultly convertible.

Organic oxygenates useful in this invention have an empirical formula which can be written:

$$C_n H_{m-2p} \cdot pH_2O$$

where $n$ is the number of carbon atoms in the molecule, $p$ is the number of oxygen atoms in the molecule and $m$ is the number of hydrogen atoms in the molecule. Difficultly convertible oxygenates, as the term is used herein, are those in which the relation:

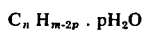

$$R = \frac{m - 2p}{n}$$

is equal to or less than 1. Easily convertible oxygenates, as the term is used herein, are those in which this relation $R$ is greater than 1.

These criteria are separate and distinct, not cumulative. That is if an aliphatic organic oxygenate is either an acid or has value of $R$ up to 1, it is considered to be difficultly convertible. Easily convertible aliphatic organic oxygenates are non-carboxylic acids having a value of $R$ greater than 1. These criteria are cumulative in that the compound must satisfy both criteria. The preferred embodiment of this invention requires the conversion of a mixture of aliphatic organic oxygenates having a total cumulative value of $R$ of greater than a stoichiometric deficiency of carboxylic acids. In a preferred embodiment of this invention, monocarboxylic acids are the difficulty convertible oxygenates and monohydric alcohols are the easily converted oxygenates. With a mixture of methanol and acetic acid, the feed should have a mole ratio of the former to the latter greater than 1, most preferably greater than 2.

Carrying out this conversion using a mixed feed as aforesaid not only improves the catalyst cycle life and yields of gasoline boiling range, particularly aromatic products obtainable from the difficulty convertible reactant, but it actually increases the yield of gasoline boiling range, particularly aromatic products at the expense of the $C_4^-$ portion of the product usually obtained from the conversion of the desirable, e.g. alcohol; reactant. Put more succinctly in perspective, the conversion of acetic acid at 500° to 1000° F over a ZSM-5 zeolite will give a product which comprises in the organic portion $C_4^-$ aliphatics and $C_5^+$ aromatics and aliphatics. It also cokes and chars the catalyst in a shorter than expected time. The conversion of methanol or dimethyl ether under the same conditions gives excellent yields of hydrocarbon products and exhibits long catalyst life with little coke slowly building up on the catalyst. The hydrocarbon products are predominantly in the gasoline boiling range with some $C_4^-$ aliphatics.

It would, of course, be desirable to carry out this conversion in such a manner as to increase the yield of gasoline boiling range hydrocarbons at the expense of the lighter, $C_4^-$ products. It is truly an unexpected advantage of co-converting lower alcohols and/or ethers etc. with acids, lower aldehydes and/or carbohydrates that not only is the conversion of these latter compounds improved, but the proportion of the hydrocarbon product which is gasoline as compared to lighter hydrocarbons is significantly increased even with respect to the already high yields of gasoline obtained from alcohol and ether conversion.

It is an important feature of this aspect of this invention therefore to co-convert easily converted and difficulty converted lower aliphatic organic compounds containing hetero atoms in order to improve the overall yield of desired full range gasoline with respect to that which is obtainable from either reactant type alone. In this regard, it is an important feature to use mixtures of single compounds, e.g. dimethyl ether and acetic acid, as the feed to this process. It is also an important feature of this invention to use multi-component mixtures, which contain more than one easily converted and/or more than one difficulty converted reactant. In fact, it may be most preferred to use a fully mixed feed such as that obtained by the controlled partial oxidation of propane, butane or naphtha in the vapor or liquid phases. Other sources of such mixtures of various light oxygenates include the Fischer-Tropsch process wherein synthesis gas, carbon monoxide and hydrogen, are catalytically converted to a mixture of lower aliphatic organic oxygenated compounds including alcohols, ethers, aldehydes, ketones, etc.

These aspects of this invention will be illustrated by the following Examples in which parts and percentages are by weight unless expressly stated to be on some other basis. The following Table sets forth the results obtained in four comparative tests run side by side under substantially identical conditions. The temperature was 700° F; the pressure was 1 Atmosphere; the space velocity was 1 LHSV; and the catalyst was H-ZSM-5 with 35% $Al_2O_3$ binder.

| | -continued |
|---|---|
| Butenes | 1.13 |
| i-Pentane | 2.76 |
| n-Pentane | 1.12 |
| Pentenes | 0.31 |
| $C_6$ + PON | 4.25 |
| Benzene | 3.30 |
| Toluene | 16.48 |
| Ethylbenzene | 2.53 |
| Xylene | 21.49 |
| $A_9$ | 15.36 |
| $A_{10}$ | 7.59 |
| $A_{11}$+ | 1.00 |
| TOTAL $C_5$+ | 76.19 |
| TOTAL AROMATICS | 67.75 |

What is claimed is:

1. In the process of converting lower aliphatic oxygen containing organic compounds of the empirical formula $C_nH_{m-2p} \cdot pH_2O$ where $n$ is the number of carbon atoms, 1 to 8, $p$ is the number of oxygen atoms and $m$

| Example No. | 1 | 2 | 3 | 4 |
|---|---|---|---|---|
| Feed (Mol %) | $CH_3OH$ (100) | $CH_3OH$ (80) S-Trioxane (20) | $CH_3OH$ (67) Acetaldehyde (33) | $CH_3OH$ (80) Acetic Acid (20) |
| Product Distribution | | | | |
| Hydrocarbons (wt %) | 45.66 | 38.02 | 46.29 | 38.72 |
| Oxygenates | 0.03 | 0.11 | 0.13 | 0.02 |
| Water | 57.76 | 50.62 | 50.40 | 55.72 |
| Carbon oxides | 0.25 | 11.20 | 2.36 | 4.44 |
| Hydrogen | 0.03 | 0.05 | 0.02 | 0.01 |
| Product Distribution Hydrocarbon portion | | | | |
| Methane | 0.42 | 1.99 | 1.03 | 1.15 |
| Ethane | 0.47 | 0.84 | 0.77 | 0.48 |
| Ethylene | 0.45 | 0.56 | 0.66 | 1.18 |
| Propane | 15.50 | 16.46 | 9.73 | 5.64 |
| Propylene | 1.27 | 1.16 | 0.89 | 0.80 |
| i-Butane | 19.16 | 12.05 | 7.00 | 3.40 |
| n-Butane | 5.29 | 3.93 | 2.96 | 1.32 |
| Butenes | 1.21 | 0.77 | 0.87 | 0.63 |
| i-Pentane | 9.40 | 3.82 | 3.00 | 2.30 |
| n-Pentane | 1.34 | 0.66 | 0.75 | 0.42 |
| Pentenes | 0.19 | 0.13 | 0.29 | 0.33 |
| $C_6$ PON | 6.02 | 2.19 | 2.70 | 2.47 |
| $C_7$ + PON | 1.78 | 0.63 | 0.98 | 0.86 |
| Benzene | 0.90 | 1.66 | 2.23 | 1.91 |
| Toluene | 7.34 | 10.32 | 12.92 | 11.05 |
| Ethylbenzene | 0.93 | 0.80 | 1.88 | 2.26 |
| Xylenes | 15.57 | 22.13 | 26.05 | 25.64 |
| $A_9$ | 9.72 | 14.45 | 18.69 | 26.01 |
| $A_{10}$ | 2.95 | 4.93 | 6.58 | 10.29 |
| $A_{11}$+ | 0.09 | 0.54 | — | 1.86 |
| Carbon Selectivity* | 99.8 | 89.2 | 98.1 | 96.3 |

*Carbon in hydrocarbon product/carbon in feed × 100

In the following Example 5, a mixture comprising 57% $C_1$–$C_6$ alkanols, 3% $C_2$–$C_4$ alkanals, 11% $C_3$–$C_6$ alkanones and 29% $C_2$–$C_5$ alkanoic acids was converted to a mixed hydrocarbon product, as indicated, using an HZSM-5 catalyst. Conditions were 1 Atm. pressure, 1 LHSV, 700° F and 3 hours total time on stream.

| TOTAL PRODUCT, Wt% | |
|---|---|
| Hydrocarbons | 58.14 |
| Oxygenates | 0.03 |
| $H_2O$ | 39.55 |
| $CO_2$ | 2.93 |
| CO | 1.53 |
| $H_2$ | 0.03 |
| | 102.21 |
| HYDROCARBONS, Wt% | |
| Methane | 0.11 |
| Ethane | 0.68 |
| Ethylene | 0.89 |
| Propane | 8.74 |
| Propylene | 1.35 |
| i-Butane | 7.50 |
| n-Butane | 3.41 | is the number of hydrogen atoms in the feed, to a product comprising water and hydrocarbons, said hydrocarbons containing a preponderance of the carbon of said organic compounds, by contacting such feed with a crystalline aluminosilicate zeolite catalyst having a silica to alumina ratio of at least about 12 and a constraint index of about 1 to 12 at an elevated temperature of at least about 500° F, and a space velocity of about 0.5 to 50 LHSV; the improvement, whereby increasing the aromaticity of said hydrocarbon product, which comprises providing as said feed a mixture of a difficultly convertible organic compound having a value of $$R = \frac{m-2p}{n}$$

of up to 1 and an easily convertible organic compound having no carboxylic acid groups and having a value of $R$ of greater than 1, said mixture having a cumulative value of R of greater than 1 and a stoichiometric deficiency of carboxylic acid groups.

2. The improved process claimed in claim 1 wherein said feed mixture comprises a carboxylic acid and a monohydric alcohol.

3. The improved process claimed in claim 1 wherein said product hydrocarbons consist essentially of $C_4^-$ light aliphatics and $C_5^+$ full boiling range, highly aromatic gasoline.

4. The improved process claimed in claim 1 wherein said feed comprises as said difficulty convertible compounds at least one member selected from the group consisting of $C_1$ or $C_2$ aldehydes, polyhydric alcohols, carboxylic acids, carbohydrates and carboxylic acid anhydrides, and as said easily convertible compounds at least one member of the group consisting of alcohols, ethers, ketones, esters of carboxylic acids and $C_3^+$ aldehydes.

5. The improved process claimed in claim 1 carried out at about 600° to 900° F.

6. The improved process claimed in claim 1 using a ZSM-5 zeolite as the catalyst.

7. The improved process claimed in claim 2 wherein said difficulty convertible material is selected from the group consisting of acetic acid, acetaldehyde and a formaldehyde moiety.

8. The improved process claimed in claim 1 including converting a mixture of acetic acid and methanol to a product comprising toluene.

* * * * *